United States Patent [19]

Harris et al.

[11] 4,353,242

[45] Oct. 12, 1982

[54] MULTICHANNEL DETECTION AND RESOLUTION OF CHROMATOGRAPHIC PEAKS

[75] Inventors: Joel M. Harris; Fritz J. Knorr, both of Salt Lake City, Utah

[73] Assignee: University of Utah Research Foundation, Salt Lake City, Utah

[21] Appl. No.: 217,283

[22] Filed: Dec. 16, 1980

[51] Int. Cl.³ .......................................... G01N 31/08
[52] U.S. Cl. .................................. 73/23.1; 73/61.1 C
[58] Field of Search ........................... 73/23.1, 61.1 C; 422/70, 89; 23/232 C; 201/1; 203/3; 364/498, 500, 501, 497

[56] References Cited

U.S. PATENT DOCUMENTS

| | | | |
|---|---|---|---|
| 3,365,931 | 1/1968 | MacRitchie et al. | 73/23.1 |
| 3,566,674 | 3/1971 | Talroze et al. | 73/23.1 |
| 3,726,127 | 4/1973 | Putnam et al. | 73/23.1 |
| 3,863,489 | 2/1975 | Ayers et al. | 73/23.1 |

Primary Examiner—Stephen A. Kreitman
Attorney, Agent, or Firm—Thorpe, North & Western

[57] ABSTRACT

A method and apparatus for resolving overlapped chromatographic peaks or other overlapped data obtained from operation of a differential migration apparatus used to analyze a substance whose composition is to be determined. The invention involves using a second analytical apparatus, such as a spectrometer, to supplement the data obtained from the basic differential migration apparatus. A multi-channel detector is used to monitor and record the various sets of data obtained from these apparatus. Data corresponding to regions of overlap identified by the apparatus are assembled in a measured data set. An estimated data set is then compiled describing the estimated migrational time behavior of each of a plurality of compounds present within the overlapped region. An identifying data set is then calculated based upon the estimated data set and the measured data set. This identifying data set contains unique identifying data, such as spectral data, corresponding to each compound present within the overlapped region. Errors in the identifying data set are minimized through an iterative process that modifies the estimated data set with each iteration. When the error is reduced to an acceptable level, the identifying data set serves to finally determine the number and identity of the compounds present within the region of overlap, i.e., resolve the overlapped peak, matrix techniques are advantageously used to handle and manipulate the large amount of data that is measured and generated. A computer may also advantageously be used to facilitate the speed and accuracy with which the matrices may be manipulated.

25 Claims, 13 Drawing Figures

MULTICHANNEL DETECTION AND RESOLUTION OF CHROMATOGRAPHIC PEAKS

BACKGROUND OF THE INVENTION

This invention relates to an improved method of qualitative and quantitative analysis, and more particularly to an improved method for resolving overlapped chromatographic peaks using multichannel detection techniques.

A recurring challenge facing the qualitative analysist is "separation," or accurately separating and identifying the individual components that are present in a mixture or substance having an unknown composition. Chromatography is one example of a well-known separation method that can be used to separate and analyze mixtures of chemical substances. Examples of other forms of separation methods include distillation, foam fractionation, adsorption, sublimination, molecular sieves, ion exchangers, membrane filtration, electro-dialysis, thermal diffusion and mass spectrometry.

Simply stated, chromatography is based upon the time it takes a specific component or substance to elute or migrate through a porous medium. For example, suppose a sample substance containing a mixture of unknown, distinct components A, B, & C is introduced into one end of a column or channel that is filled with a porous medium (the porous medium often being referred to as the stationery phase). The physical and chemical properties of each of the components A, B, and C, in conjunction with the physical and chemical properties of the porous medium, cause a specific migration time (often referred to as the "retention time") to be associated with each component as it flows to the other end of the column or channel. Thus, whereas all three components are placed or injected into one end of the column (or channel) simultaneously, component A may arrive at the other end of the column one minute after injection, component B three minutes after injection, and component C five minutes after injection. By knowing in advance which components migrate through the column within the one minute time window, the three minute time window, and the five minute time window (which knowledge is generally obtained experimentally using known compounds and, once obtained for a given column and porous medium, is cataloged for future reference), the unknown compounds A, B, and C can be identified. This identification assumes, of course, that a suitable detector is employed at one end of the column to detect the arrival time of each compound, and that migration time data has been previously obtained for each compound present. It also assumes that two distinct compounds do not share the same migration time, i.e., arrive at the detector within the same time window. The detector can also be used to quantitatively measure the relative concentrations of each compound within the mixture.

Chromatography may theoretically be used to analyse gases, liquids, and solids. A widely used form of chromatography in practice is gas-liquid chromatography, wherein the stationary phase is a liquid, and the mobile phase—that phase that either carries or contains the mixture of unknown compounds—is a gas. Because of its popularity, gas-liquid chromatography is often referred to as simply gas chromatography, or "GC". However, other forms of chromatography, such as liquid-liquid chromatography, are not uncommon.

While gas chromatography is an excellent tool for the separation, detection, and quantification of the components of a complex mixture, it is not, by itself, a good tool for quantitative identification. This is because there may be many thousands of compounds that may share the same retention time, thereby eluting or migrating within the same time period. The use of two or more columns, each having different retention indexes, has proven to be a viable solution to this common retention-time problem only for simple mixtures or pure compounds. Thus, because a large number of compounds share the same retention-time, effective qualitative analysis requires either a wealth of a prior information concerning what compounds are most likely to be present (thereby allowing the exclusion of compounds not likely to be present) or the combination of gas chromatography with some other separation method. In the latter case, confirmation by two or more methods is desirable. A common choice of an additional separation technique to supplement chromatography is mass spectrometry, or "MS". This is because of its high sensitivity and relatively specific spectral information.

In its simplest form, mass spectrometry consists of taking the compound to be identified and, in the gas phase, breaking it up into its constituent ions. These ions are then sorted and counted as a function of their mass. The output of a mass spectrometor thus provides specific data concerning the relative concentrations of mass-identified ions within the compound. As such, it serves as a unique "finger-print" of the compound, and can effectively be used to identify the presence of the compound within the sample mixture being analysed.

Combining mass spectrometry with gas chromatrography—a combination known as GC-MS—provides a powerful analytical tool. The gas chromatography provides an initial separation of the compounds as a function of retention time. The mass spectrometer then provides a positive identification of one of several compounds that could exhibit the measured retention time. In practice the GC-MS method is realized by connecting the output of the gas chromatographic column, through a suitable interface, to the input of a mass spectrometer. The compound that elutes or migrates from the chromatographic column within a given time window, which compound could be one of thousands of possible compounds, is then immediately exposed to the mass spectrometer for further analysis. Based on the mass spectrum obtained through this analysis, the compound (through a comparison of its measured spectrum to a catalog of spectrums) can usually be positively identified.

Despite the powerful analytical tool provided by the GC-MS combination (and similar combinations, such as gas or liquid chromatography coupled with infrared spectrum analysis, referred to as GC-IR or LC-IR respectively), a serious deficiency is encountered when two or more compounds having the same, or very close to the same, retention times are simultaneously present in the mixture. This condition is termed "overlapped chromatographic peaks" and the problem of identifying the compounds that are present within the overlap region is the specific problem addressed by this invention.

The problem of resolving overlapped chromatographic peaks can be more fully appreciated, especially by those unskilled in the art, through reference to a simple "bomb-blast" analogy. If a desk, for example, is blown up into a "million" pieces by a bomb blast, and if most of the pieces of the desk can be located and collected, a careful analysis of the pieces will generally reveal the identity of the original item, i.e., a desk. If, on the other hand, a desk, table, and chair are all simultaneously blown up by a bomb blast, and even if most of the resulting pieces are located and collected, it would be an almost impossible task to determine the identity of the original items, especially if there were no prior knowledge as to the number of items originally present. Moreover, even if it were known that there were originally three items, one of which was a desk, it would be extremely difficult to determine which pieces belonged to the desk and which did not, especially if the desk, table and chair were all made from the same or similar material.

The above bomb-blast analogy reflects, in a very simplified way, the problem facing an analyst who is attempting to identify the compounds present in an overlapped chromatographic peak, using, for example, mass spectrometry. That is, two or more compounds are present within the peak. When these compounds are "blasted apart" by breaking them up into their constituent ions, the analyst has no accurate method of determining which ions belong to which compound, unless he has prior information concerning which compounds are present. Thus, no single identifying spectrum can be obtained.

Prior art methods for interpreting spectral data obtained from overlapped chromatographic peaks have been fraught with limitations. These methods, especially as used in connection with GC-MS, have in common the recognition that the spectral pattern of a particular compound from a multi-channel detector will rise and fall in unison when one compound elutes. Accordingly, if the chromatographic data indicates the presence of two or more peaks within a given time window, one prior art separation method presumes that one peak belongs to only one compound, that one being the "sharpest" within the particular time window. After identifying the sharpest peak, the method then identifies the spectral channels which follow the same time behavior using a correlation criterion. All the spectral channels which follow reasonably well are assigned to that single component having the sharpest peak. Any channels which do not correlate are presumed to below to a different component. By subtracting out the spectral data following the time behavior of the sharpest peak, it thus becomes possible to unscramble the mixed spectral data.

The above described prior art method may be referred to as the "template approach" because it assumes that the shape of the over-lapped peak is known. This shape—or the "template"—is then presumed to belong to the same component and subtracted out. The main problem associated with this approach is in defining the "template." That is, it is difficult to accurately measure the "sharpest peak," especially if a truly complex mixture is being analysed (one in which two or more compounds are likely to be truly overlapped, having little separation between them). Also, it is highly unlikely that each compound in a particular time window can be represented by totally resolved spectral channels.

An alternative method for resolving overlapped data peaks consists of comparing the spectra of mixtures resulting from the overlapped peaks to a library of spectra of compounds that could be present. A probability based matching system using a large collection of reference spectra then determines which compound is most likely present in the mixture, subtracts the spectrum of that compound from the mixture data, and the remaining spectra are matched to the library to see whether any other compounds can be identified. This process continues until no new compounds can be matched, or until the remaining data drops below the noise level. The problems associated with this approach relate to having a priori information concerning what compounds are likely to be present. Moreover, there are always inefficiencies related to the handling of large amounts of data. Even with modern computer based systems, the data must be gathered, cataloged, and entered into the system, and once there, it must be retrievably stored. All this requires a considerable investment of time and money. Further, it is unlikely that all the compounds in a sample will be present in the library. In addition, what data is present in the library will be biased with the "signature" of the instrument through which the data was obtained.

SUMMARY OF THE INVENTION

A principle object of the present invention is to provide an improved method of qualitative and quantitative analysis for identifying and quantifying the constituent compounds or elements of a complex mixture.

A further object of the present invention is to provide such a method that is especially suited for resolving overlapped chomatographic peaks using data obtained from multi-channel detectors.

Still another object of the present invention is to provide such a resolution method that does not require reliance upon a priori information as to what compounds or elements are likely to be present in the mixture to be analysed.

Another object of the invention is to provide a resolution method that is not dependent upon knowing or locating a unique peak in the multichannel data which serves as an identifying "template" for locating other related data peaks.

An additional object of the invention is to provide a method that does not require a library, catalog, or file of reference spectra of possible mixtures, which reference spectra inherently contain the undesirable "signature" of the particular instrument which took the data contained therein.

A further object of the present invention is to provide a separation method that significantly improves existing multichannel instrumentation with respect to its capabilities for resolving ovelapped chromatographic peaks.

The above and other objects of the invention are realized in an illustrative method and apparatus that employs multi-channel detection to resolve overlapped chromatographic peaks by constructing a shape dependent upon assumed parameters for each chromatographic peak of each compound observed or assumed to be present within each time window. This constructed shape may be based either on theory (e.g., a Guassian function) or practice (e.g., a model of the instrument response function observed during the elution of a pure compound). Preferably, the constructed shape will be dependent upon a minimum number of parameters, thereby facilitating modification thereof. Optimally, only one parameter, such as the retention time, will determine the constructed shape. Once this constructed shape is determined, it serves as the basis, along with the measured "mixed" spectral data obtained by the multi-channel detector within a given time window, for determining the individual spectra associated with each compound assumed present within the time window. After these individual spectra are determined, the accuracy of the assumed parameters (such as the retention times) for each peak are tested. This testing is done by combining the individual determined spectral data of each compound to form a first set of mixed spectral data for the time period of interest (i.e., within the overlapped peak region). This first set of mixed spectral data is then compared to the measured set of mixed spectral data obtained from the multichannel detector. The assumed parameters (e.g., the retention times) of the individual peaks associated with each compound are then adjusted to minimize the error, or differences, between the first set and measured set of data, thereby forming a second, corrected, set of mixed spectral data. This adjustment process is repeated a sufficient number of times, during which third, fourth, and subsequent sets of mixed spectral data may be generated (each set being a more refined, corrected set than its predecessor) until the error is reduced to an acceptable level. Once the error between the $n^{th}$ set of mixed spectral data and the measured set of mixed spectral data has been minimized in this fashion, a sufficiently accurate set of individual spectra results. These individual spectra are then used to identify the specific compounds that are present within the overlapped peak region.

BRIEF DESCRIPTION OF THE DRAWINGS

The above and other objects, features, and advantages of the invention will be more apparent from the following more particular description presented in connection with the accompanying drawings, in which:

FIG. 8(a) is the mass spectra of a 2-ethylnaphthalene compound obtained from the isolated compound, while FIG. 8(b) is a mass spectra obtained from the specific example referred to in connection with FIG. 7;

DETAILED DESCRIPTION OF THE INVENTION

Figure 1:
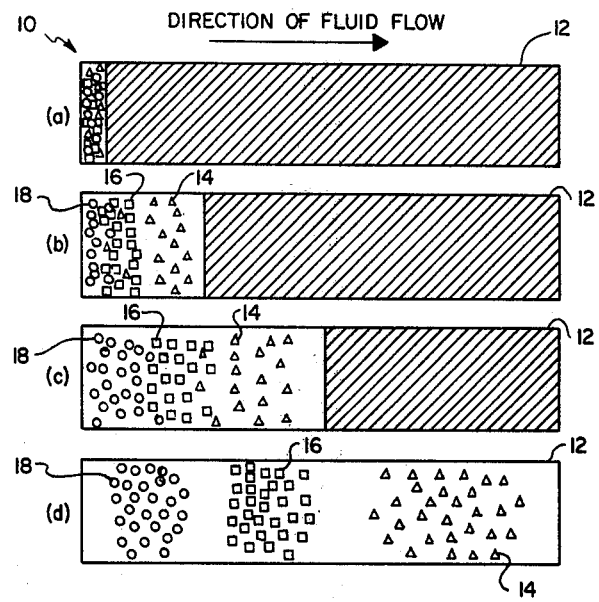
FIG. 1 is a simplified sequential drawing teaching the manner in which a mixture of compounds separates within a chromatographic column or channel.

In order to fully appreciate and understand the present invention, it will be helpful to review some basic separation principles. Reference is first made, therefore, to FIG. 1 which depicts, in simplified form, a sequential event diagram showing the separation of three compounds within a chromatographic column. It should be noted at the outset that chromatography is merely one example of the broader "differential migration methods." See generally, Karger, Snyder & Horvath, *An Introduction to Separation Science*, 106–65 (John Wiley & Sons, 1973). Accordingly, the disclosure contained herein relating to the resolution of overlapped chromatographic peaks could be used in connection with any other suitable differential migration method that yields overlapped peaks.

In the chromatography example of FIG. 1, a sample mixture 10 is caused to migrate through a porous medium contained in a column 12, or other suitable bed, by fluid flow. (Other differential migration methods, such as electrophoresis, ultracentrifugation, and field-flow fractrometron, cause the same mixture to migrate across a homogeneous region by application of a force field). The porous medium is often referred to as the "stationary phase," while the sample mixture 10 is either by itself, or suspended within, a carrier medium referred to as the "mobile phase." The sample mixture 10 undergoes an equilibrium distribution between these two phases. This equilibrium determines the velocity with which each component of the sample migrates through the system. This time of migration, in turn, may be referred to as the "retention time," for it describes the time a given compound is retained in the stationary phase. Compounds that reach an equilibrium distribution primarily in one phase (stationary or mobile) thus move at a different rate than compounds that are distributed primarily in the other phase.

Differences in migration rate, or retention times, can lead to the separation of mixed components as depicted in FIG. 1. In FIG. 1, the sample mixture 10 contains three components. A first component 14 is represented symbolically as a group of small triangles, a second component 16 as a group of small squares, and a third component 18 as a group of small circles. As the sample mixture 10 is initially introduced into the column 12, the components 14, 16, and 18 are all mixed together, as shown in the top sequence (a) of FIG. 1. A short time later, as each of the components begins to reach its respective equilibrium distribution, separation of the components begins to occur, as shown in sequence (b) of FIG. 1. In FIG. 1 (b) component 14 has begun to migrate through the column 12 at a faster rate than components 16 and 18, and component 16 has begun to migrate at a faster time than component 18, although some bunching of all the components still persists. In sequence FIG. 1 (c), on the other hand, the components have almost separated with only a little overlap remaining between each group. Finally, in sequence FIG. 1 (d), the different migration rates, or retention times, of the three components have led to their complete separation.

Figure 2:
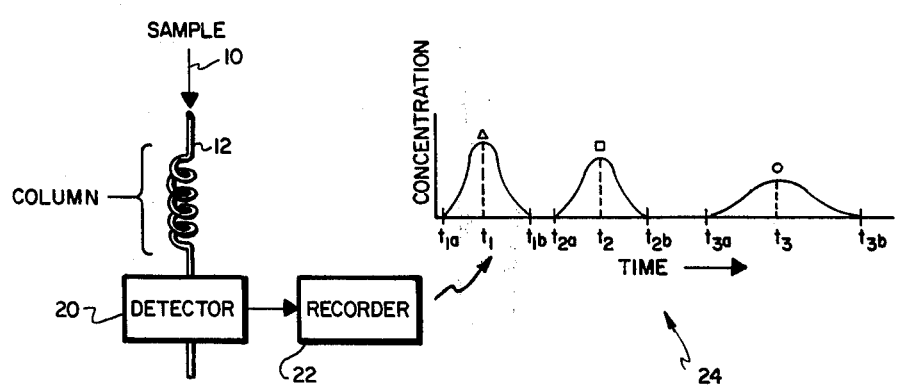
FIG. 2 is a block diagram illustrating the basic elements of a chromatographic system, and also depicting the type of data obtained therefrom.

FIG. 2 shows a block diagram of a chromatographic system and illustrates the type of data obtained therefrom. The system includes a column 12 into which a sample mixture 10 is injected. A detector 20 is positioned at the opposite end of the column 12 from where the mixture 10 is introduced. This detector 20 senses the presence and concentration of components flowing therethrough. Thus, when coupled with a recorder 22, data of the type shown generlly at 24 may be obtained. This data indicates the time at which a given component of the sample mixture 10 arrives at the detector 20 (measured relative to the time the sample is injected into the column 12), and indicates the relative concentration of that component at that arrival time. Thus, assuming the same three component mixture 10 discussed in connection with FIG. 1, the component 14, which migrates through the column 12 in the shortest time, arrives first at the detector 20 at time $t_1$. Similarly, component 16 arrives next at the detector at time $t_2$, and component 18 arrives last at the detector at time $t_3$. The times $t_1$, $t_2$, and $t_3$ are thus the "retention times" associated with the components 14, 16, and 18 respectively.

It is important to note that all portions of component 14 do not all arrive at the detector 20 at time $t_1$. Rather, as component 14 migrates through the column 12, it disperses into a zone wherein various concentrations of the component 14 can be found. This zone dispersion is often Gaussian. Hence, at time $t_{1a}$, the front edge of the zone of component 14 begins to reach the detector 20. For Gaussian dispersed zones, this front edge represents a very light concentration of component 14. This concentration steady increases, however, until at time $t_1$ the highest concentration of component 14 arrives at the detector. This is the peak of the zone dispersion. After time $t_1$, the concentration steadily decreases until at time $t_{1b}$, the trailing edge of the zone finally arrives at the detector. Hence, some levels of concentration of component 14 are continually sensed within the time window defined by the times $t_{1b}-t_{1a}$. Similar time windows defined by the times $t_{2b}-t_{2a}$ and $t_{3b}-t_{ca}$ exist in which some levels of concentration of components 16 and 18 respectively are continually sensed.

Several different chromatographic methods exist. For example, chromatographic methods may be classified according to: (1) type of mobile and stationary phases (e.g., gas or liquid); (2) the mechanism by which the individual components are retained in the phases (e.g. sorption—including adsorption or partition—or exclusion); (3) the technique (column or open bed); and (4) the method of sample development or component movement through the column or bed (e.g., elution, frontal, or displacement). Gas chromatography which is based on adsorption in a column through which the components elute is perhaps the most common method of chromatography used at present. However, the preceding paragraphs describing FIGS. 1 and 2 apply equally well to any chromatographic method, and indeed, any differential migration method, that may be employed.

Figure 3:
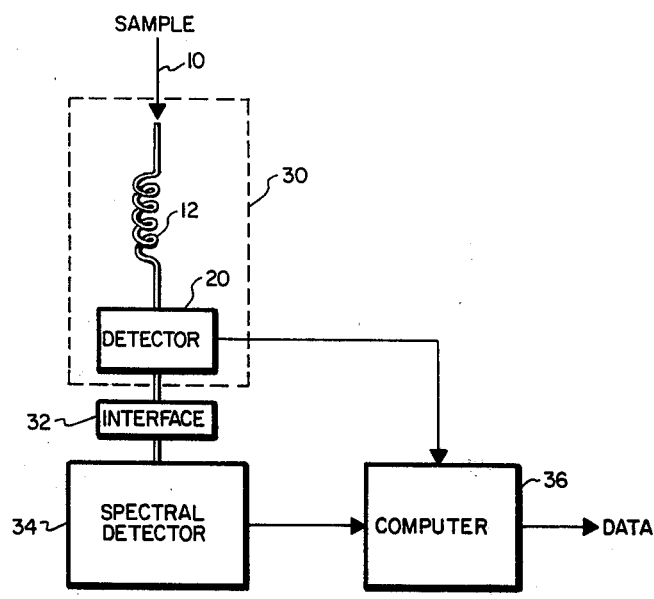
FIG. 3 shows a simplified block diagram of a GC-MS system (a system using both chromatography and a mass spectrometer), exemplary of the types of systems that may be utilized by this invention.
Figure 4:
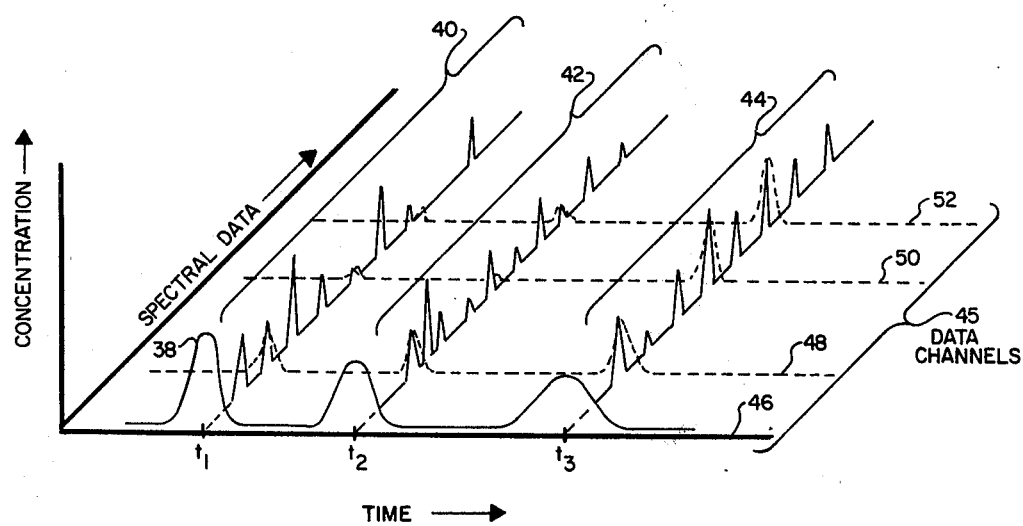
FIG. 4 illustrates a three dimensional graphical representation of the types of data sets obtained from the GC-MS system of FIG. 3 or any similar multichannel detection method.

The retention time of a given component, or its migration time through a stationary phase is a column or bed having a fixed length, is a characteristic trait that may be used to identify a given component. Unfortunately, as mentioned earlier, several components may exhibit the same or similar retention times, making it difficult or impossible to positively identify the compound unless prior knowledge exists as to which compounds are likely to be present in mixture. To overcome this difficulty, it is often helpful to employ a second analytical method to augment the analysis performed by a first analytical method (such as chromatography). One approach for using two analytical methods to analyse the composition of an unknown mixture is shown in FIG. 3. The type of data obtained from the method of FIG. 3 is illustrated in FIG. 4. The dual method shown in FIG. 3 incorporates a chromatographic system 30, including a column 12 and a detector 20, an interface unit 32, a spectrometer 34, and a data handling unit 36, such as a computer or functionally equivalent data handling device (including manual data handling methods). When the chromatographic system 30 is gas chromatography, and the spectrometer 34 is a mass spectrometer, the resulting analytical method is referred to as GC-MS. GC-MS represents only one method of several that are available wherein two separate analytical methods are combined via appropriate interfaces. See Hirschfield, "The Hy-phen-ated Methods," 52 Analytical Chemistry 297A (February 1980). A computer is typically used as a backup with all such combined systems to tie everything together (although conceptually anything the computer does could be achieved through manual or semimanual methods).

A spectrometer, such as the spectrometer 34 of FIG. 3, produces spectral data that is a function of the composition of a sample compound (or mixture of compounds) at the time the spectral data is obtained. The spectral data may indicate the intensity distribution of masses contained within the sample, as in the case of a mass spectrometer, or the data may indicate refractive indices, radiant intensities, wavelengths, and the like, obtained when the sample itself is subjected to a radiant energy source.

Whatever the nature of the spectral data, it is significant to note that it is time invariant. That is, the spectral data is purely a function of the composition of the sample being analysed. However, when the composition of the sample is a function of time, as is the case when the sample is a function of time, as is the case when the sample is first obtained from the column 12 of a chromatographic system 30 (FIG. 3), a different set of spectral data may be obtained for each time period of concern. Thus, in FIG. 4, a first chromatographic peak 38 may be obtained from the chromatographic system 30 (FIG. 3) at retention time $t_1$. At time $t_1$, the sample present at the output of the chromatographic column 12 may be further analysed by subjecting it to the spectrometer 30. The spectrometer 30 generates a set of spectral data 40 based on the make-up of the particular compound or component that has separated from the mixture 10 at retention time $t_1$. Knowing the measured retention time $t_1$ will narrow the list of possible compounds or components that could be present in the mixture significantly. Coupling this knowledge with the measured time invariant spectral data 40 will then usually suffice to positively identify which of all possible components having retention time $t_1$ is present within the mixture.

In a similar fashion, sets of time invariant spectral data 42 and 44 may be obtained to positively identify which of all possible components having retention times $t_2$ and $t_3$ respectively are present within the sample mixture 10. It should be emphasized that while FIG. 4 indicates only one set of spectral data being taken for each chromatographic peak, there could be several sets of spectral data taken during a given time window of interest, each spectral set of data corresponding to a different time within the time window. For example, the spectromer 34 could be configured to sample and analyse the effluent from the chromatographic column 12 at a periodic rate having a frequency f, thereby generating a complete set of spectral data every T seconds, where T is 1/f. Each set of spectral data thus generated could be further monitored and recorded at a specific point along the spectrum on one of a plurality of data channels 45. Three of such channels 48, 50, and 52 are illustrated in FIG. 4. Hence, including the main chromatographic data channel 46, four data channels, each monitoring specific data as a function of time, are depicted in FIG. 4. Any number of data channels, of course, could be used. The use of more than one data channel in this fashion is often referred to as "multi-channel detection." Understandably, the use of a computer 36 (FIG. 3) greatly facilitates the monitoring and handling of the large amounts of data that result when multi-channel detection is employed.

Figure 5:
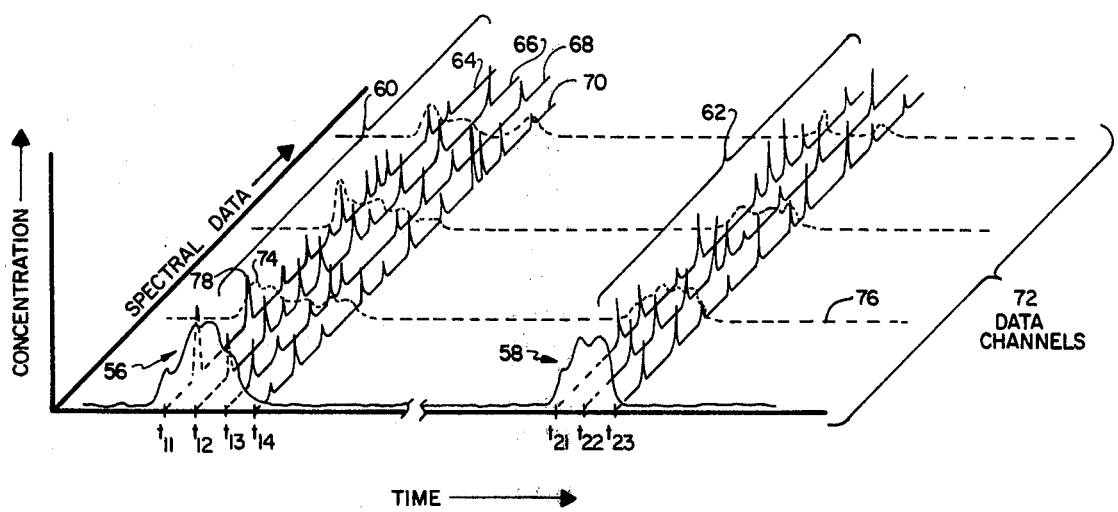
FIG. 5 illustrates a three dimensional graphical representation of the types of data sets obtained from a multichannel detection system when two or more compounds are present within a given time window.

Referring now to FIG. 5, there is shown the specific problem that occurs when two or more components or compounds separate from the sample mixture within the same time window. This is the problem of overlapped chromatographic peaks, and two of such overlapped peaks, 56 and 58, are depicted in FIG. 5. Also depicted in FIG. 5 are the sets of spectral data 60 and 62 that might illustratively be obtained from a periodic sampling of the overlapped peaks 56 and 58 respectively. Referring to the overlapped peak 56, for example, a single set 64 of spectral data is obtained at retention time $t_{11}$. Similarly, single sets of spectral data 66, 68, and 70 are obtained at retention times $t_{12}$, $t_{13}$, and $t_{14}$ respectively. While these individual spectra accurately reflect the composition of the sample at their respective retention times, the sample being analysed at these times remains a composite, or mixture, of several compounds or components due to the overlapped condition. Therefore, without having prior knowledge as to how much of each individual spectra is attributable to a known component, it is extremely difficult, using present methods, to unscramble the spectral data to a point where it can be used to identify the individual compounds or components that are present within the overlapped peak. Moreover, as seen in FIG. 5, the use of several data channels 72 does not necessarily improve the resolution problem associated with overlapped peaks. This is because an overlapped condition is likely to exist on each data channel, and without prior information to the contrary, it would have to be assumed that the specific spectral data contained in each peak of each data channel 72 results from the presence of more than one compound. In this regard, it must be kept in mind that the separation process associated with chromatography and other differential migration methods is a gradual process, rather than a discrete process. Accordingly, as discussed in connection with FIG. 2, various concentrations of a given compound are distributed within the time window of concern. Periodic spectral data taken within the time window necessarily reflects these various levels of concentration. Thus, while a specific peak 74 occurring in the data channel 76 at time $t_{11}$ may be the result of an identifiable spectral line or peak 78 appearing in the set 64 of spectral data, it is still uncertain which compound, or combination of compounds, was originally responsible for the spectral line or peak 78. For example, assuming the overlapped chromatographic peak 56 is comprised of four separate compounds W, X, Y, and Z, it is possible that 75% of spectral line 78 is attributable to component W, 15% to component X, 8% to component Y, and 2% to component A. On the other hand, 99% of spectral line 78 may be attributable to component X and 1% to component Y. Without prior knowledge, therefore, as to likely concentrations of each component, it is essentially impossible to sufficiently unscramble the spectral data so that it can be used for identifying components present within the overlapped region.

The present invention recognizes that measured multi-channel data within a region of chromatrographic overlap (or other differential migration area of overlap) reflects the sum of all the individual spectral data sets, or other identifying data sets, associated with each component present within the overlapped region. These identifiable, unscrambled, data sets can be determined from the measured scrambled data set if the time behavior associated with the differential migration of each compound within the overlapped region is known. The resolution method of the present invention assumes a function for their time behavior, thereby defining a shape for each compound suspected of being present within the time window of concern. Identifiable individual data sets are then determined for each compound using a small number of parameters to specify the shape. Once determined, these individual data sets are then combined, or scrambled, to produce a first data set for the region of overlap. This first data set corresponds to the already measured scrambled data set for the same region. If the assumed parameters have been accurately selected, the two scrambled data sets will be equal. Accordingly, the first data set is compared to the measured data set and the difference, or error, between the two is determined. The assumed parameters are then modified to minimize this difference or error. A sufficient number of iterations are performed using this process until a desirable degree of accuracy is obtained.

Figure 6:
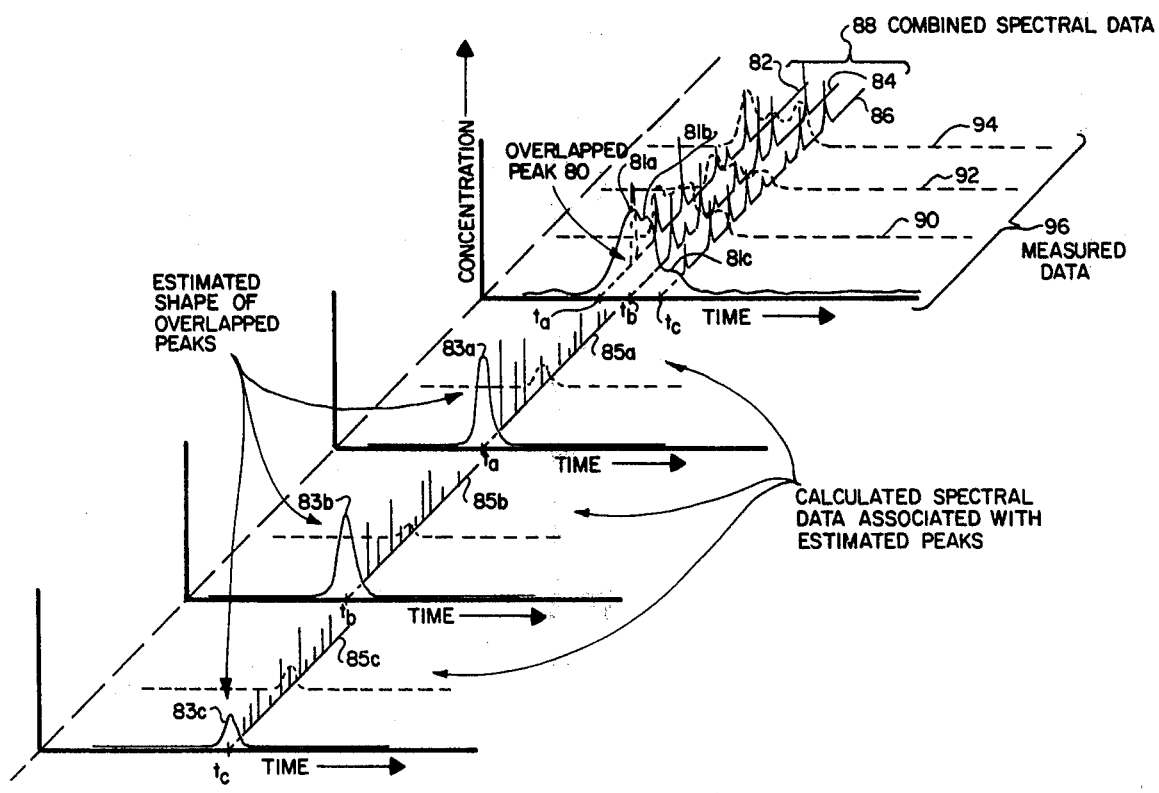
FIG. 6 also illustrates a three dimensional graphical representation of the types of data sets obtained when an overlap condition exists, and further symbolically depicts the results of the separation method employed by the present invention.

The above process is symbolically illustrated in FIG. 6. A first analytical method, such as chromatography, produces a data peak 80 that appears to be comprised of overlapped individual data peaks 81a, 81b, and 81c. This overlap reflects the composition of the sample mixture that is being analysed. A second analytical technique, such as spectral analysis, produces additional data sets 82, 84, and 86 corresponding to specific times within the overlapped region. The data contained in these data sets 82, 84, and 86 represents a measured combined spectral data set 88 of the mixture being analysed. This data set 88 may be monitored and measured on several channels simultaneously, such as channels 90, 92, and 94, thereby producing a set of measured data 96. Either data set 88 or data set 96 (or a combination of both data sets) may be thought of as the measured "scrambled" data.

Still referring to FIG. 6, three distinct peaks are initially presumed present within the overlapped region, each peak resulting from the presence of a separate component within the mixture being analyzed. This initial presumption of three components is based upon the general appearance of the chromatographic data. As will be more fully set forth below, an attractive feature of the invention herein disclosed allows such an initial estimate of the number of compounds present to be made. This estimate may be subsequently verified and, if necessary, revised. Thus, even if it's not initially clear from the overlapped data how many compounds are involved, the method allows any number of compounds to be initially assumed.

Parameters defining a shape are initially assigned to each of the peaks associated with each component presumed present. This shape reflects the best estimate of the time behavior of each compound within the region of overlap. As such, it represents the shape that would be detected if that particular compound were the only one present. This shape may initially be modeled as Gaussian. Alternatively, it may be modeled based upon the observed instrument response function of the particular chromatographic detection equipment that is used. Whichever method is used, a first peak 83a is modeled to present the best estimate of the time behavior associated with the component responsible for the overlapped peak 81a observed in the data peak 80. Similarly, second and third peaks 83b and 83c are modeled as the best estimates of the time behavior of the components responsible for overlapped peaks 81b and 81c respectively. Once these initial estimates of the time behavior are made, corresponding spectral data 83a, 83b and 83c may be determined for each peak. This determination assumes that the measured data 96 (or 88) is the sum of the individual data sets 85a, 85b, and 85c. Thus, by having defined an initial estimate of the shapes of the individual peaks 83a, 83b, and 83c, and by knowing the set of measured data 96 (or 88), it is possible to make an initial determination as to the individual data sets 85a, 85b, and 85c. Once determined, these data sets are combined to see if they produce a first scrambled data set that is the same as, or close to, the measured scrambled data set 96 (or 88). If not, the prior estimates of the parameters defining the shapes of the peaks 83a, 83b, and 83c, are varied, new sets of data sets 85a, 85b, and 85c are re-determined, and a new or second, scrambled data set is produced. This second scrambled data set should be closer to the measured scrambled data set 96 (or 88) providing the modifications to the parameters defining the peaks 83a, 83b, and 83c have been properly made. A proper modification is one in a direction that minimizes the error between the first (or second, third, and so on) scrambled data set (comprised of data sets 85a, 85b, and 85c) and the measured scrambled data set 96 (or 88). Once this error has been minimized below an acceptable and specified level, the individual determined data sets 85a, 85b, and 85c may be used to identify the components present within the overlapped peak 80. Moreover, the entire process may now be repeated, if desired, assuming a different number of components are present within the overlapped region to verify the correctness of the number of compounds assumed present. For example, if the initial number of components were estimated at three, the whole process could be repeated assuming four compounds are present. If the minimum error obtainable assuming four compounds, properly weighted for the loss in degrees of freedom, is significantly greater than that obtained assuming three compounds, then three is the correct number of compounds. If, however, the achievable error is less assuming four compounds, then four is the correct number of compounds. This verification process can be used as many times as is required to ensure that the correct number of compounds has been determined. Preferably, the initial estimate of compounds will be a low number, such as two or three, thereby allowing succeeding estimates to be increased by one until the minimum error point is found.

The above described identification process is easily made using a minimum of computation without the necessity of having a priori knowledge as to the composition of the mixture being analyzed, and without the need to maintain and refer to extensive data libraries describing various possible combinations of components that are likely to be present.

With the preceding overview in mind, a more detailed description of the invention will now be given. A first step is to collect and assemble the multi-channel data in a usable format. The data itself may be gathered using any of a number of commercially available measurement and analytical equipment. An exemplary set of such equipment, for a GC-MS analysis, includes the model 5991 GC/MS Data System manufactured by Hewlett-Packard. Because a large amount of data may be involved, a preferred method is to assemble this measured data in a matrix, designated (for convenience purposes) as the [D] matrix. The [D] matrix contains the measured scrambled data arranged in a format corresponding to the order in which the data was measured. Thus, each column of the [D] matrix would contain a different set of time data, such as the sets 90, 92, and 94 of FIG. 6. Each element of each column would, in turn, represent an individual data point taken at a specific time. Each row of [D], on the other hand, would contain a different set of spectral data, such as the sets 82, 84, and 86 of FIG. 6. [D] thus becomes an x, spectral channel, by t, time channel matrix, where x and t are integers.

The method disclosed in this application unscrambles or decomposes the [D] matrix into its constituent data elements without relying on a priori knowledge as to what compounds would most likely produce the measured set of scrambled data, and without relying on large libraries or previously stored data to discover possible combinations that could have produced the measured sets of scrambled data. The [D] matrix is considered to be composed of the sum of the spectra (or other time invariant data) of the individual compounds in the sample mixture weighted by their concentration at each time the data is obtained. This relationship is most conveniently expressed in Equation (1) as:

$$[A][C]=[D] \tag{1}$$

where [A] is an x by n matrix containing the spectra of the n individual components in its columns, and [C] is an n by t matrix containing the elution behavior (or retention time behavior, equilibrium behavior, or other time variant behavior) of the individual compounds in its rows. Decomposing [D] into [A] and [C] thus becomes a significant step of the resolution method herein disclosed.

Once the [D] matrix has been assembled, the next step is to estimate, or model, the [D] matrix. This estimate is designated as the [C'] matrix. It contains the relative time behavior of the chromatographic peaks of different retention tmes in each of its tows. Formulating the [C'] matrix thus initially involves a determination as to how many compounds n are included within the overlapped region. This determination can usually be accurately made from a cursory inspection of the chromatographic (or other differential migration) data. In FIG. 6, for example, it is apparent that the overlapped peak 80 contains three "humps," indicating the presence of at least three compounds in the mixture. Hence, for the example depicted in FIG. 6, the method would initially assume that n is three. However, as mentioned previously, this is only an initial estimate that can subsequently be verified. If, for example one of the humps were wider than the others, it could indicate the presence of two compounds within the same hump. Accordingly, after performing the analysis with n=3, it would be advisable to perform the analysis again with n=4. If a lower error weighted by the degrees of freedom in the fit is obtained with n=4 than was obtained with n=3, then four is the right value to use. (Note, it would even be advisable to try n=5 to further verify that n=4 is correct.)

After the value of n is determined, either from an inspection of the overlapped data or by some other means, (which value indicates the number of rows that will be present within the [C'] estimated matrix), the relative time behavior, or shape, of the chromatographic peaks (or other differential migration peaks) associated with each component is estimated. This estimate is described in the columns of the [C'] matrix. Thus, each column of [C'] contains a numerical description of the shape, or time behavior, of one of the n compounds estimated to be present within the overlapped peak.

As mentioned earlier, there are at least two methods that can be used to estimate the shape of the peak of the individual compounds. First, the time behavior of the peaks can easily and accurately be modeled as Gaussian functions, since the width and position of a Gaussian peak is dependant only on one variable, the retention time, $t_R$. That is, $$S = t_R/N \qquad (2)$$

where S is the standard deviation (width) of the Gaussian peak, and N is the number of theoretical plates in the chromatographic column (which can be easily determined from the peak shape and amplitude of a single compound that is passed through the column). The retention time, $t_R$, is estimated from the measured time at which the peak occurs within the overlapped region. Thus, referring to the example of FIG. 5, the retention time of the compound associated with the peak 81a would be estimated as $t_a$, the measured time at which the peak occurs. Similarly, the retention times of the compounds associated with the peaks 81b and 81c would be estimated as $t_b$ and $t_c$ respectively. The shape of the modeled peaks 83a, 83b, and 83c would then be modeled as a Gaussian function about these retention times.

The second method than can be used to estimate the shape of the peak of the individual compounds, such as the shape of peaks 83a, 83b, and 83c in the example of FIG. 6, is to model the shape from the "instrument response" function of the particular instruments that are used in obtaining the chromatographic (or other differential migration) data. That is, the chromatographic (or other data) may clearly indicate that the measured response is non-Gaussian. Such non-Gaussian behavior could be caused by a variety of reasons, e.g., dead volume, adsorption, etc. If such non-Gaussian behavior is observed, a pure sample could then be eluded through the column and the peak shape thus observed could serve as the initial model for the peak shapes to be estimated. The width of this instrument function could then be adjusted to account for the variation in instrument response as a function of retention time.

In practice, a combination of both methods above described could be used to estimate the shape of the peak of the individual compounds. That is, the models of the Gaussian functions could be convoluted with a single-sided exponential to account for the tailing due to extra-column dead volume. See, e.g., Lochmuller & Sumner, 18 J. Chromatog. Sci. 159-65 (1980). The tailing decay time could be readily determined from the instrument response function measured using a pure sample, which instrument response function could simultaneously be used to determine the number of theoretical plates as above described.

Having thus determined an initial estimate of the [C'] matrix, either theoretically or with a measured instrument function, or with a combustion of theoretical and measured methods, an estimate of the [A] matrix may be determined by substituting the estimated [C'] matrix into Equation (1) for the [C] matrix and solving for the [A] matrix. Because such a calculation is based upon only an estimate of the [C] matrix, the solution will likewise be only an estimate, and accordingly is designated as [A']. Thus, the matrix equation to be initially solved is:

$$[A'][C'] = [D] \qquad (3)$$

Several matrix techniques could be employed to solve Equation (3). However, the preferred method is to obtain [A'] by using a right psuedo inverse of [C'], or a Householder transmation. Doing so, [A'] is found to be expressed as:

$$[A'] = [D][C']^T([C'][C']^T)^{-1} \qquad (4)$$

The [A'] matrix obtained from Equation (4) thus represents an initial estimate of the spectral (or other time invariant) data of the n individual compounds suspected of being present within the mixture being analyzed. The actual computation solution of Equation (4) is, of course, most easily performed using a computer.

To test the goodness of fit of the [A'] and [C'] matrices to the true [A] and [C] matrices, the estimated [C'] matrix and calculated [A'] matrix are multiplied together (i.e., the individual data contained therein are mixed or scrambled together as it would be within a region of overlap) to form an initial [D'] matrix. That is, matrix multiplication yields $$[A'][C'] = [D'] \qquad (5)$$

If [A'] and [C'] are accurate representations of the true [A] and [C] matrices, then the initial, or first, [D'] matrix calculated in Equation (5) should be equal to, or very nearly equal to, the [D] matrix of Equation (1). (Recall that the [D] matrix is the actual measured data within the region of overlap.) Thus, the difference, or error, between the [D'] and [D] matrices represents a good measure of the accuracy of the [A'] and [C'] matrices. This difference, or error $x^2$, is most effectively determined using a sum-of-squares technique such as that described by Equation (6):

$$X^2 = \frac{1}{xt - n(x+1)} \sum_{i=1}^{x} \sum_{j=1}^{t} (D_{ij} - D'_{ij})^2$$

Based on the value of the sum-of-squares error determined by Equation (6), the retention times (which control the shape and position of corresponding data peaks) for the individual components used in the construction of the [C'] matrix are then varied in order to minimize the error. A new [A'] matrix, based on the revised [C'] matrix, is then determined, thereby allowing a revised, or second, [D'] matrix to be compiled. Based on this second [D'] matrix, the error is again determined. This process is repeated a sufficient number of times, each iteration resulting in new and refined [C'], [A'] and [D']

matrices, until the error as measured by Equation (6) is reduced below an acceptable level.

As a further aid to reducing the error between the [D'] and [D] matrices, an additional penalty may be imposed whenever negative amplitudes are found to exist within the [A'] matrix. Negative values appearing in the [A'] matrix generally indicates a large error was made in initially assigning values to the [C'] matrix. Accordingly, by singling out the specific points where negative data appear, and weighing these points with an appropriate constant, $P_{neg}$ (typically a number from 1-100), the sum-of-squares minimization technique above referred to in connection with Equation (6) may be modified so that the errors originally responsible for generating the negative values are quickly minimized. An appropriate process for penalizing negative data in this fashion can be readily devised by those skilled in the art.

Having minimized the error through the above described iterative process, the final [A'] and [C'] matrices thus represent a good fit to the true [A] and [C] matrices. Assuming that the correctness of the value of n, or number of components, has also been verified by comparing the relative error of the [D'] matrix for various values of n as above described, these final [A'] and [C]' matrices can thus be used as an accurate representation of the decomposition, or unscrambling, of the measured [D] matrix. In particular, the final [A'] matrix will contain the spectral (or other time invariant) data of each of the n compounds present within the mixture. Thus, an additional step to the method disclosed herein is to use the finally arrived at [A'] matrix to specifically identify the compounds which are present within the overlapped region.

From the results obtained thus far with the above described method, it appears to the inventors that only one parameter—the retention time—need be varied for each compound in the mixture in order to reduce the error below an acceptable level. However, even though only one parameter is varied, a multiparameter result—the spectrum—is obtained. Thus, an added feature of the invention herein disclosed is the favorable ratio of information produced (an entire spectrum) relative to the effort expended (varying one parameter).

The method disclosed herein is also advantageous in that the correct value of n, the number of components present within the mixture, is readily determined. If the above data matrix procedure is carried out for increasing values of n, one can expect the minimum error found to continue to decrease so long as n is too small. This is becase the peak shapes that are used to model the [C'] matrix typically represent a low pass filter of the time information that can be added to [D'] in an effort to obtain [D]. As long as the value of n is too low, there will be low frequency features in the residuals matrix which can only be corrected by allowing the number of components to increase to the proper value. If the temporal model used in the fit is correct, then, when n is the proper value, only high frequency random noise is left in the residuals matrix. The contribution of this noise to the error cannot significantly be decreased by further increasing n due to the low frequency nature of the model. As a result, the error does not decrease further by increasing n beyond its true value.

This approach to determining the number of components in the mixture is an attractive alternative to prior art methods (which typically attempt to identify the number of independent contributing functions in the data set using factor or principal component analysis). The major problem with these prior art methods is the fact that the eigenvectors of the covariance matrix, which are determined, have no relationship to the actual function form of the physical process. The approach disclosed herein, on the other hand, searches for an optimum fit to the data using, as a basis set, functions which are the proper representations of the physical system. As a result, the determination of n is much less sensitive to noise, which is the most independent function in any real data set.

The resolution method described herein has successfully performed separation of major components having a high degree of chromatographic and spectral overlap. See Example described below. Moreover, the method does not depend on the particular multichannel detector used as long as a linear response is obtained (i.e., as long as Equation (1) can be satisfied). Thus, the method disclosed by this application could provide a significant improvement for detection methods such as IR, UV-VIS, and fluorescence, where the likelihood of spectral overlap is even greater than for mass spectrometry. In sum the method could be applied to any number of "hy-phen-ated" analytical methods, see Hirschfield, "The Hy-phen-ated Methods," supra, where a linear response is observed.

EXAMPLE

To illustrate the method of separation of severely overlapped mixtures as described above, the following example is presented:

Repetitively scanned GC-MS data were gathered on binary and ternary mixtures of poorly resolved compounds. The mixtures used were: (1) 0.05 M 1,3-dimethylnaphthalene, 0.05 M 2-ethylnaphthalene, and 0.05 M 2,6-dimethylquinoline in $CH_2Cl_2$; (2) 0.05 M 1,3 dimethylnaphthalene, 0.05 M 2-ethylnaphthalene in acetone; and (3) 0.07 M 3-methylcyclohexanol, 0.05 M 1-heptanol and 0.05 M 3-methylcyclohexanone in $CH_2Cl_2$. The mass spectra of the individual components of these mixtures were gathered under identical instrumental conditions to compare the spectral separated by numerical means.

The chromatograph was a 3 ft.×2 mm. i.d. glass column packed with 1% OV 17 on Chromosorb W, interfaced to the mass spectrometer through a jet separator. The naphthalene mixture was eluted with an initial column temperature=130 C, temperature programmed at 20 C/min starting at injection time. The ketone-alcohol mixture was eluted at initial temperature=30 C., programmed at 20 C/min. Injector temperature was 225 C. 1.0 uL volumes of the mixtures were injected. Helium carrier gas flow rate was 18 ml/min.

The mass spectrometer system was an LKB 9000S interfaced to a DEC PDP 11/40 running RT-11 V2 operating system which controlled spectrometer functions and data aquisition. Ion source pressure was $2\times10^{-6}$ torr; ion source temperature was 250 C. Electron energy was 70 V and electron trap current was 60 $\mu$A. Repetitive scanning period for this system was a relatively slow 5 sec.

The repetitively scanned GC-MS data were copied to magnetic tape, and the data manipulation described here was performed on a DEC PDP 11/45 running RSX-11M operating system With this system, it was possible to manipulate up to 30 by 30 data matrices. Matrices were formed from time windows of width less than or equal to 30 scans; m/e channels of negligible intensity were deleted until the number of rows was less than or equal to 30.

The chromatographic system parameters, N, the number of theoretical plates, and $\tau$, the exponential tailing decay time, were evaluated from the total ion current signal measured for the elution of a pure compound. The standard deviation, of the underlying Gaussian and the exponential decay parameter, $\tau$, were calculated from the second and third moment of the peak as previously described by Lochmuller and Sumner, supra. The chromatographic system typically exhibited 750 theoretical plates and a tailing decay time of approximately 8 seconds. To guide the search method in finding the correct spectra, the penalty constant for negative spectral values was set at $P_{neg}=100$. Values of $P_{neg}$ as small as 1 still allowed the data to be separated, but the spectral assignments were significantly poorer.

Figure 7:
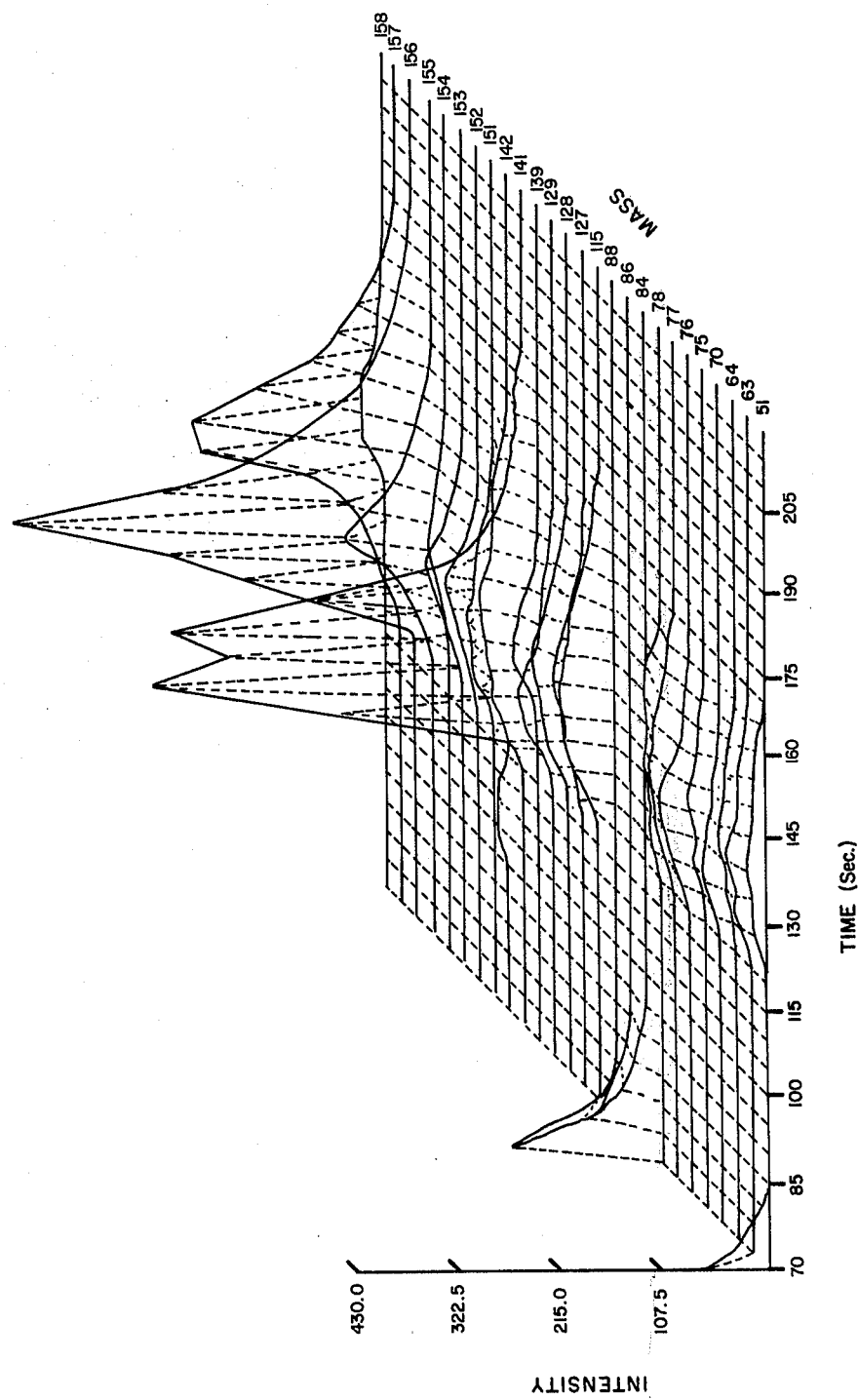
FIG. 7 is an actual GC-MS data matrix of a ternarynaphthalene mixture used in connection with a specific resolution example cited below in the detailed description of the invention.

The GC-MS data matrix for the ternary naphthalene mixture, 2-ethylnaphthalene, 1,3-dimethylnaphthalene, and 2,6-dimethylquinoline, is shown in FIG. 7. The solvent tailing into the time window is apparent to the left. It is clear that the signals from the analytes are severely overlapped. Application of the data analysis procedure, while incrementing the value of n, was successful in identifying the correct number of components. The value of the error, $\chi^2$, as determined using Equation (6), decreased rapidly until the proper value of n was used to construct [C'] as shown below in Table 1. Further increases of n do not reduce $\chi hu\ 2$, since the fit does not improve any faster than the loss of degrees of freedom. In Table 1, the values of $\chi hu\ 2$ are scaled to the minimum value found, and the comparison of $\chi^2$ is actually compared to $(n-1)$, rather than n inasmuch as the solvent peak tailing into the data matrix, which comprises a distinct analyte component in the mixture (and therefore increases n by one), is easily separated out by the process.

TABLE I

| | Values of $\chi^2$ (scaled) versus (n − 1) | | | |
|---|---|---|---|---|
| Mixture (number of analytes) | 1 | 2 | 3 | 4 |
| 1. Naphthalenes (3) | 9.45 | 3.78 | 1.00 | 1.14 |
| 2. Naphthalenes (2) | 1.58 | 1.00 | 1.04 | 1.02 |
| 3. Alcohols-Ketone (3) | 20.77 | 2.31 | 1.00 | 1.00 |

Figure 8:
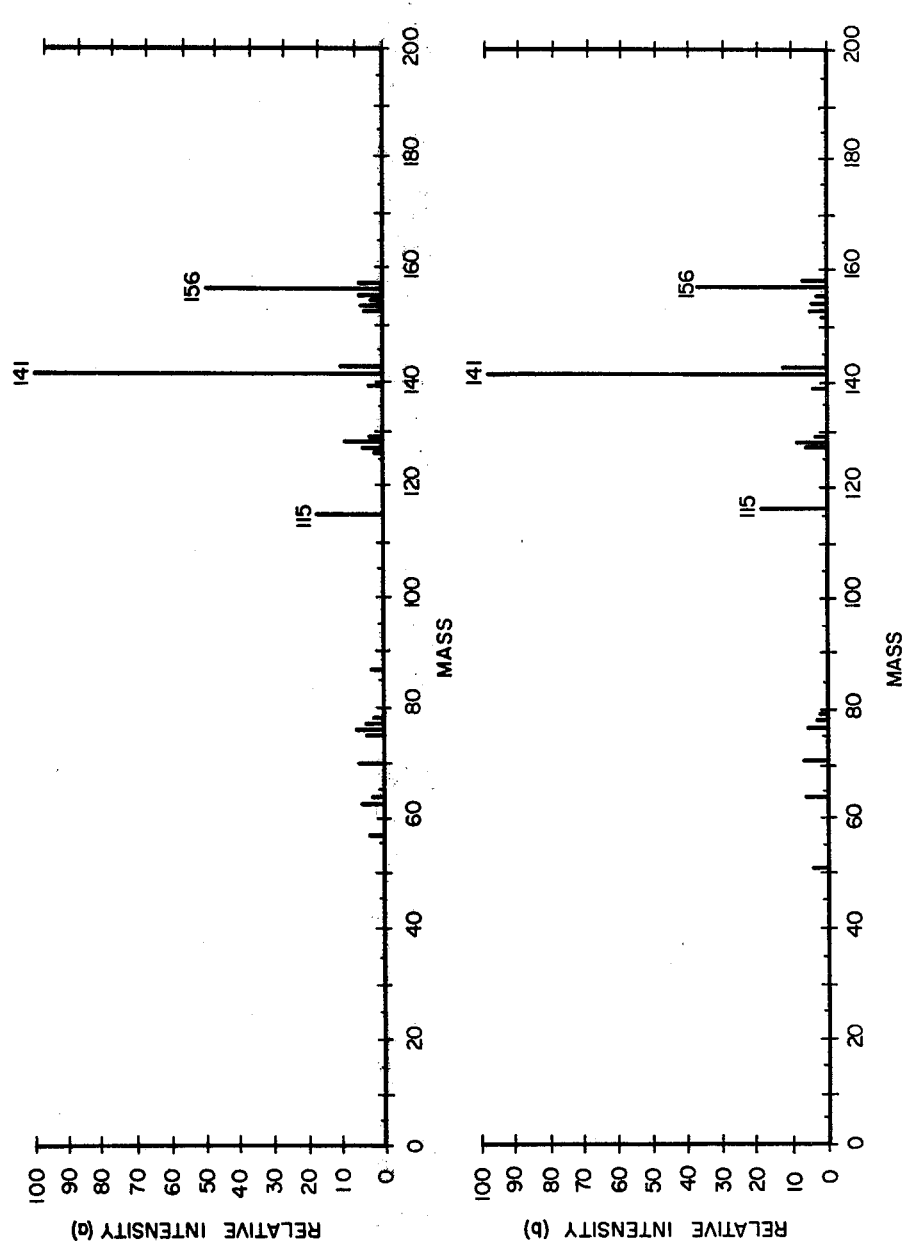
Figure 9:
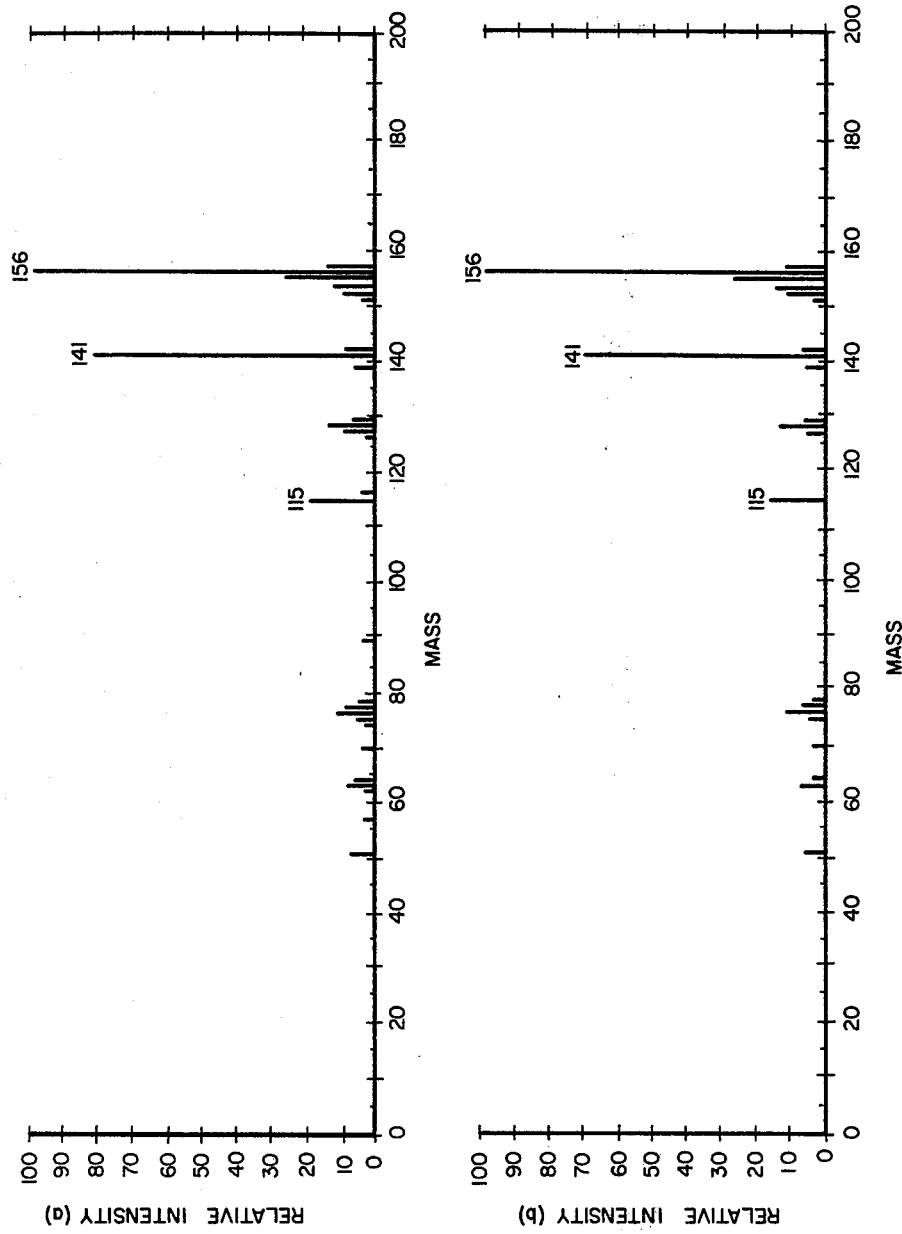
FIGS. 9(a) and 9(b) are respectively the same as FIGS. 8(a) and 8(b) except that the compound is 1,3-dimethylnaphthalene.
Figure 10:
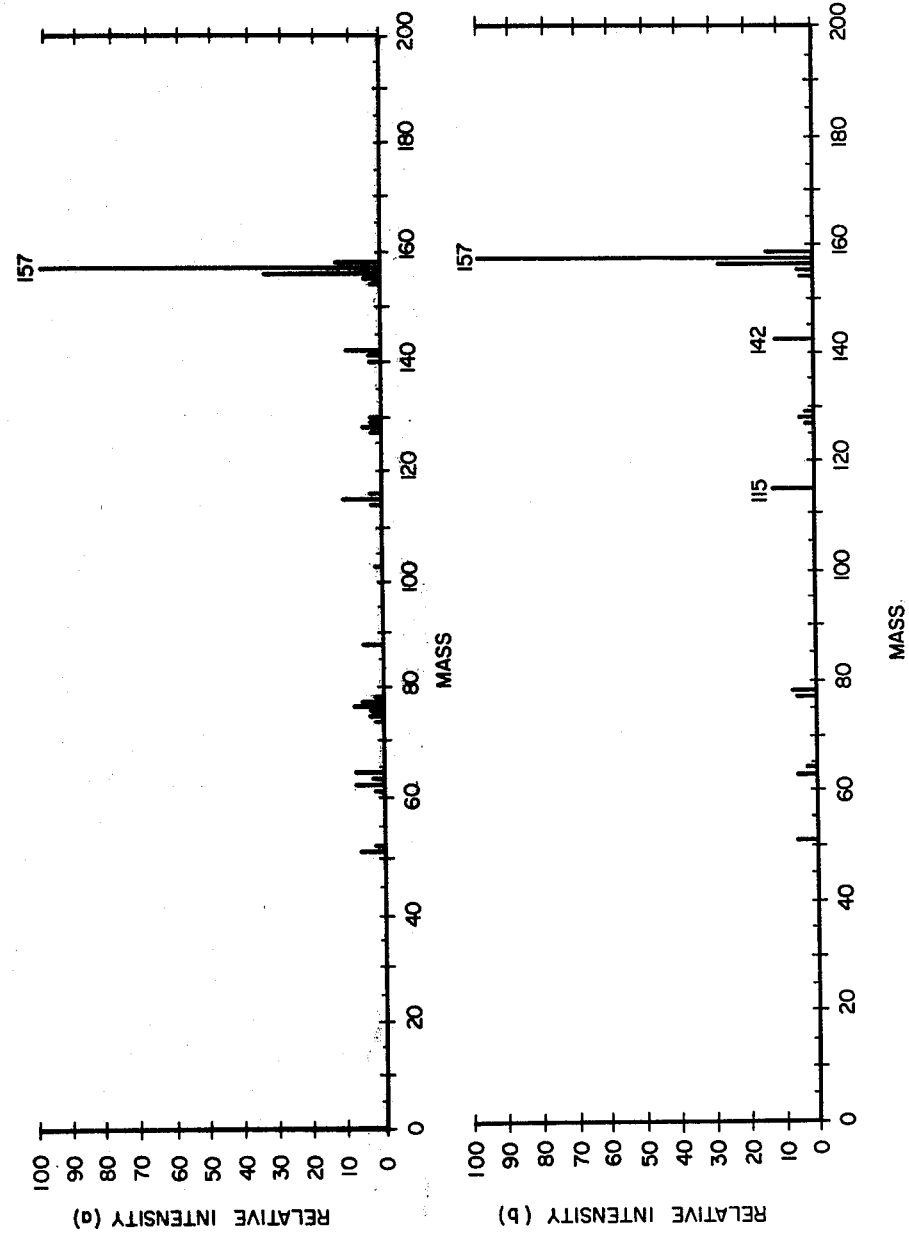
FIGS. 10(a) and 10(b) are respectively the same as FIGS. 8(a) and 8(b) except that the compound is 2,6-dimethylquinoline.

If the correct number of components are used to construct the [C'] matrix, and the retention times are adjusted for a minimum $\chi^2$, then the normalized spectra of the individual components should occupy the columns of the matrix, [A'], factored from the data by the the pseudoinverse of [C']. The spectra taken from [A'] are shown in FIGS. 8(b), 9(b) and 10(b). For comparison, the spectra of the isolated components gathered on the instrument under identical conditions are respectively shown in FIGS. 8(a), 9(a), and 10(a). The major features of the spectra have clearly been resolved successfully, even though none of the three components has significant mass peak which is unique. The relative error in the spectra, numerically resolved from the data matrix, were determined by comparison with the spectra of the isolated components, as shown below in Table II. In Table II, $t_R(s)$ represents time of the identified component in seconds. The relative error is shown as a percentage that was computed by adding the absolute values of the spectral errors and normalizing this sum to the total spectral amplitude. Several masses represented in each of the isolated component spectra are missing in the numerically resolved spectra since several of the lowest intensity mass channels in the original data have been deleted in constructing the data matrix, in order to keep the matrix within the limits of the memory size. In calculating the relative error in the spectra, only those mass channels represented in the data matrix are used so as not to bias the results by a technical limitation. On the average, the deleted mass problem would contribute an additional 4% relative error to the results reported.

TABLE II

| Mixture | Component | $t_R$ (s) | Rel. [A] error (%) |
|---|---|---|---|
| (1) | 2-ethylnaphthalene | 128 | 15 |
| | 1,3-dimethylnaphthalene | 138 | 8 |
| | 2,6-dimethylquinoline | 152 | 10 |
| (2) | 2-ethylnaphthalene | 127 | 13 |
| | 1,3-dimethylnaphthalene | 135 | 10 |
| (3) | 3-methylcyclohexanol | 62 | 21 |
| | 1-heptanol | 66 | 23 |
| | 3-methylcyclohexanone | 78 | 7 |

Numerous other examples could be cited. However, for purposes of this patent application, it is felt that the method and apparatus of the invention has been adequately disclosed and taught so that it can be understood and practiced by those skilled in the art.

While the invention herein disclosed has been described by means of specific sequences, steps, and applications thereof, numerous modifications could be made thereto by those skilled in the art without departing from the spirit and scope of the present invention. It is therefore to be understood that within the scope of the appended claims, the invention may be practiced otherwise than as specifically described herein.

What is claimed is:

1. A method for resolving overlapped migration data obtained while performing qualitative analysis of a substance whose composition is to be determined, said method comprising the steps of:

(a) subjecting said substance to be analysed to a first apparatus adapted to separate compounds contained in said substance as a function of their respective migration time in a given medium, said first apparatus further adapted to provide a set of migration data indicating the migration behavior of said compounds as a function of time;

(b) subjecting samples of said substance at specified times relative to the initiating of step (a) to a second apparatus, said second apparatus being adapted to measure and provide a unique set of characterizing time-invariant data for each of said samples, said set of characterizing data being a function of all the compounds contained in said sample at said specified times;

(c) identifying regions of peak overlap within said set of migration data, said regions of overlap indicating the presence within said sample of at least two compounds having approximately the same differential migration times;

(d) estimating a data set describing the differential migration time behavior of each of the compounds suspected of being present within each region of overlap identified in step (c), said set of estimated time behavior data describing the estimated shape of the migrational response of each said compounds within said region of overlap;

(e) calculating a set of identifying time-invariant data for each of said compounds suspected of being present within said regions of overlap from said measured sets of characterizing data and said estimated sets of time behavior data;
(f) varifying the goodness of the estimate made in step (d) by:
  (i) combining the calculated sets of identifying data derived in step (e) with the corresponding sets of estimated time behavior data made in step (d),
  (ii) comparing said combination of said estimated and calculated data to said measured set of characterizing data obtained in step (b), and
  (iii) determining an error factor based on said comparison:
(g) modifying the estimated time behavior data made in step (d) as a function of the magnitude of the error factor determined in step (f);
(h) repeating steps (e), (f), and (g) as many times as is necessary in order to reduce the error factor calculated in step (f)(iii) to an acceptable level; and
(i) identifying the compounds present within said region of overlap based upon the last set of calculated identifying data obtained in step (e) as a result of the repetition of step (h).

2. A method as defined in claim 1 wherein said overlapped differential migration data comprises overlapped chromatographic peaks, said first apparatus comprises a chromatographic detector, and said differential migration time of each compound comprises a retention time associated with said compound within said chromatographic detector.

3. A method as defined in claim 2 wherein said second apparatus comprises a spectral detector adapted to produce a spectrum of each of said samples at said specified times.

4. A method as defined in claim 3 wherein step (d) of estimating the time behavior of each of the compounds comprises estimating a Gaussian shaped chromatographic peak centered about the respective retention time of each of said compounds.

5. A method as defined in claim 3 wherein the step of estimating the time behavior of each of the compounds referred to in step (d) comprises estimating a shape for the chromatographic peak that is determined from the instrument response function of the apparatus used to obtain the data, said instrument response function shape being coincident with, at least in part, the respective retention time of each of said compounds.

6. A method as defined in claim 3 wherein the step (d) comprises estimating a modified Gaussian shaped chromatograhpic peak for each compound centered about the respective retention time of each of said compounds, said modified Gaussian shape including a Gaussian peak modified with a tailing function that is determined from the instrument response function of the detectors used to obtain the data.

7. A method as defined in claims 4, 5 or 6 wherein said spectral detector is a mass spectrometer.

8. A method as defined in claims 4, 5, or 6 wherein said spectral detector is an infrared spectrometer.

9. A method as defined in claims 4, 5, or 6 wherein step (g) of modifying the estimated time behavior data comprises modifying the retention time associated with each compound.

10. A method for resolving overlapped chromatographic peaks of a substance being analysed, said substance having a plurality of unknown compounds mixed therewithin, said method comprising the steps of:

(a) injecting said substance to be analysed into a first end of a chromatographic column;
(b) monitoring the output of said chromatographic column at a second end thereof with a first detector, said first detector being adapted to provide a first set of data indicating the migrational time behavior of the mixture of compounds through said column;
(c) subjecting, in periodic fashion, samples of said substance to a second detector after said samples have passed through said column, said second detector being adapted to provide unique sets of time-invariant characterizing data, each set thereof being a function of the particular combination of said plurality of compounds preset within said sample at the time said sample is analysed by said second detector;
(d) monitoring and recording said sets of time-invariant data and said first set of data using multi-channel detection means;
(e) identifying regions of overlap within said first set of data wherein at least two of said plurality of compounds have migrated through the column within approximately the same time period;
(f) assembling the sets of time-invariant data corresponding to said identified regions of overlap into a [D] matrix;
(g) constructing a [C] matrix containing an estimate of the time behavior of each of said plurality of compounds within each identified region of overlap, said estimate being based upon time-behavior estimation means;
(h) calculating an [A] matrix that is a function of said [D] and [C] matrices, said [A] matrix indicating a single set of time-invariant characterizing data for each of said plurality of compounds present within said region of overlap, the relationship between [A], [C], and [D] matrices being [A][C]=[D];
(i) testing the accuracy of said [A] matrix by multiplying said [A] and [C] matrices to form a [D'] matrix, and by comparing said [D'] matrix to said [D] matrix, the difference between the [D'] and [D] matrices indicating a measure of the error present in the [A] matrix;
(j) miminizing the error in the [A] matrix by using said measure of the error determined in step (i) to guide a modification to the [C] matrix, using said modified [C] matrix to recalculate the [A] matrix as was done in step (h), and testing the accuracy of the re-calculated [A] matrix as was done in step (i);
(k) repeating step (j) as many times as is required to reduce said error in the [A] matrix below a specified limit; and
(l) using the [A] matrix having the error minimized therein as a identifier of the individual compounds of said plurality of compounds that are present within said substance within said region of overlap.

11. A method for resolving overlapped chromatographic peaks as defined in claim 10 wherein said chromatographic column comprises a column employed in gas chromatography.

12. A method for resolving overlapped chromatographic peaks as defined in claim 10 wherein said second detector of step (c) comprises a spectrometer, and said sets of time-in-variant data comprise spectral data of said samples.

13. A method for resolving overlapped chromatographic peaks as defined in claim 12 wherein said spectrometer is a mass spectrometer.

14. A method for resolving overlapped chromatographic peaks as defined in claim 10 wherein siad time-behavior estimation means of step (f) comprises assuming the time behavior of each of said compounds to be Gaussian centered about a peak in the migrational time behavior observed in step (b), said peak occurring at a specific retention time.

15. A method for resolving overlapped chromatographic peaks as defined in claim 10 wherein said time-behavior estimation means of step (f) comprises modeling the time behavior of each of said compounds after a measured instrument response function of the multi-channel detection means of step (d), said instrument response function being defined about a retention time.

16. A method as defined in claim 14 wherein the Gaussian time behavior is modified to include a tailing function representative of the instrument response function of the multi-channel detection means of step (d).

17. A method for resolving overlapped chromatographic peaks as defined in claims 13, 14, or 15 wherein the modification to the [C] matrix in step (j) comprises modifying a single parameter corresponding to each compound, said single parameter being the retention time.

18. A method for resolving overlapped chromatographic peaks as defined in claim 10 wherein the calculation of said [A] matrix in step (h) comprises calculating [A] based on the following matrix equation:

$$[A]=[D][C]^T([C][C]^T)^{-1}.$$

19. A method for resolving overlapped chromtographic peaks as defined in claim 10 wherein the minimizing of the error in the [A] matrix in step (j) includes the utilization of a sum-of-squares technique.

20. A method for resolving overlapped chromatographic peaks as defined in claim 10 wherein a computer is used to aid in the monitoring, recording, and assembling of said sets of data, as well as in the matrix computations employed in calculating and minimizing the error within the [A] matrix.

21. A method for determining the number of compounds present within overlapped migration data of a substance having a plurality of unknown compounds mixed therewithin, said method comprising the steps of:
(a) subjecting said substance to first apparatus adapted to separate compounds contained in said substance as a function of their respective differential migration time in a given medium, said first apparatus further adapted to provide a set of migration data indicating the migration behavior of said compounds as a function of time;
(b) subjecting samples of said substance at specified times relative to the initiating of step (a) to a second apparatus, said second apparatus being adapted to measure and provide a unique set of characterizing time-invariant data for each of said samples, said set of characterizing data being a function of all the compounds contained in said sample at said specified times;
(c) identifying regions of peak overlap within said set of migration data, said regions of overlap indicating the presence within said sample of two or more compounds having approximately the same migration times;
assuming the number of compounds present within each region of overlap identified in step (c) to be a low integer, n;
(e) estimating a data set describing the differential migration time behavior of each of the compounds suspected of being present within each region of overlap identified in step (d), said set of estimated time behavior data describing the estimated shape of the migrational response of each said compounds within said region of overlap;
(f) calculating a set of identifying time-invariant data for each of said compounds suspected of being present within said regions of overlap from said measured sets of characterizing data and said estimated sets of time behavior data;
(g) determining an error factor representing the correctness of the number of compounds present within each region of overlap by:
  (i) combining the calculated sets of identifying data derived in step (f) with the corresponding sets of estimated time behavior data made in step (e),
  (ii) comparing said combination of said estimated and calculated data to said measured set of characterizing data obtained in step (b), and
  (iii) determining an error factor based on said comparison;
(i) comparing the last determined error factor from the most recent performance of step (g) with the next-to-last determined error factor obtained from the next-to-most recent performance of step (g);
(j) repeating steps (e), (f), (g), (h), and (i) until the error factors compared in step (i) remain essentially the same; and
(k) assigning as the correct number of compounds present within the substance the last value of n from step (h).

22. An apparatus for resolving overlapped chromatographic peaks of a substance being analysed, said substance having a plurality of unknown compounds mixed therewithin that need to be identified, said apparatus comprising:
a chromatographic column;
means for injecting said substance to be analysed into a first end of said column;
first detector means coupled to a second end of said column for providing a first set of data indicating the migrational time behavior of said mixture of compounds through said column;
second detector means coupled through an interface unit to said first detector means for providing a plurality of second sets of data, said second detector means adapted to analyse, in periodic fashion, samples of said substance after said samples have passed through said column and said interface unit, said analysis of said second detector means resulting in said second sets of data, each set thereof providing unique time-invariant characterizing data that is a function of the particular combination of said plurality of compounds present within said sample at the time said sample is analysed by said second detector means;
multi-channel detection means for monitoring and recording said first set of data and said second sets of data;
means for identifying regions of overlap within said first set of data wherein at least two of said plurality of compounds have migrated through the column within approximately the same time period;
means for assembling the sets of time-invariant data recorded by said multi-channel detection means corresponding to said identified regions of overlap into a [D] matrix;
time-behavior estimation means for constructing a [C] matrix containing an estimate of the time behavior of each of said plurality of compounds within each identified region of overlap;

calculation means for calculating an [A] matrix that is a function of said [D] and [C] matrices, said [A] matrix indicating a single set of time-invariant identifying data for each of said plurality of compounds present within said region of overlap;

error minimization means for minimizing any error contained within said [A] matrix as a result of inaccuries in the time behavior estimates of said [C] matrix, said means for minimizing error comprising:

means for multiplying said [A] and [C] matrices to form a [D] product matrix, means for comparing the difference between said [D'] and [D] matrices, said difference indicating a measure of the error present within said [A] matrix, means for updating the timer behavior estimates contained in the [C] matrix as a function of the magnitude of said error found in said [A] matrix, and means for recalculating said [A] matrix based upon said updated [C] matrix;

means for repeating the updating and recalculating the [C] and [A] matrices respectively using said error minimization means until the error contained within the [A] matrix is reduced below an acceptable level; and means for applying analysing the identifying data contained within the error-minimized [A] matrix to identify the specific compounds of said plurality of compounds that are present within said substance within said region of overlap.

23. An apparatus for resolving overlapped chromatographic peaks as defined in claim 22 wherein said multichannel detection means comprises a computer coupled to said first detection means and second detection means.

24. An apparatus for resolving overlapped chromatographic peaks as defined in claim 22 wherein said second detector means comprises a spectrometer.

25. An apparatus for resolving overlapped chromatographic peaks as defined in claim 24 wherein said time estimation means comprises:

means for determining a retention time for each compound present within said region of overlap, said retention time corresponding to a peak in said first set of data;

means for defining the migrational time behavior of each compound about said retention time.

* * * * *